United States Patent [19]

Lalui

[11] Patent Number: 5,540,234
[45] Date of Patent: Jul. 30, 1996

[54] PEAK FLOW METERS

[75] Inventor: Ardawan Lalui, Ennis, Ireland

[73] Assignee: Vitalograph (Ireland) Limited, County Clare, Ireland

[21] Appl. No.: 346,180

[22] Filed: Nov. 22, 1994

[30] Foreign Application Priority Data

Nov. 29, 1993 [GB] United Kingdom .................. 9324455

[51] Int. Cl.$^6$ ..................................................... A61B 5/093
[52] U.S. Cl. .............................. 128/725; 128/727; 482/13
[58] Field of Search ..................................... 128/725, 726, 128/727; 482/13

[56] References Cited

U.S. PATENT DOCUMENTS

| 4,499,905 | 2/1985 | Greenberg et al. | 128/727 |
| 5,246,010 | 9/1993 | Gazzara et al. | 128/725 |
| 5,320,107 | 6/1994 | O'Brien | 128/725 |

FOREIGN PATENT DOCUMENTS

| 2247838 | 3/1992 | United Kingdom | 128/725 |

OTHER PUBLICATIONS

Asthma in the School–Improved Control with Peak Flow Monitoring by G. Mendoza, M.D.; M. K. Garcia, R.N.; and M. A. Collins, M.A.; cover sheet and p. 35.

Peak Flow Monitoring for Patents with Asthma, Georgetown University CIRID, Published by Healthscan, Inc., 1990, cover sheets & p. 9.

Personal Best Peak Flow Meter, product description panel, Healthscan Products, Inc., 1993.

*Primary Examiner*—Lee S. Cohen
*Attorney, Agent, or Firm*—Breiner & Breiner

[57] ABSTRACT

A peak flow meter consists in known fashion of a housing having in it a channel along which a pointer (6) is movable to a distance dependent on the lung function of a patient using the meter. Positioned adjacent the channel are two or more indicators (12) movable along an axis parallel with the channel. Each indicator is preferably shielded from manual contact, and e.g. is movable along its path only by use of a tool. In accordance with the invention, each indicator presents to view two visually-distinguishable areas defining a boundary (24) which can be set at a point along the path of the pointer to indicate limit positions relating to lung function, so as to indicate graphically to the user when he or she might need to take remedial action.

9 Claims, 7 Drawing Sheets

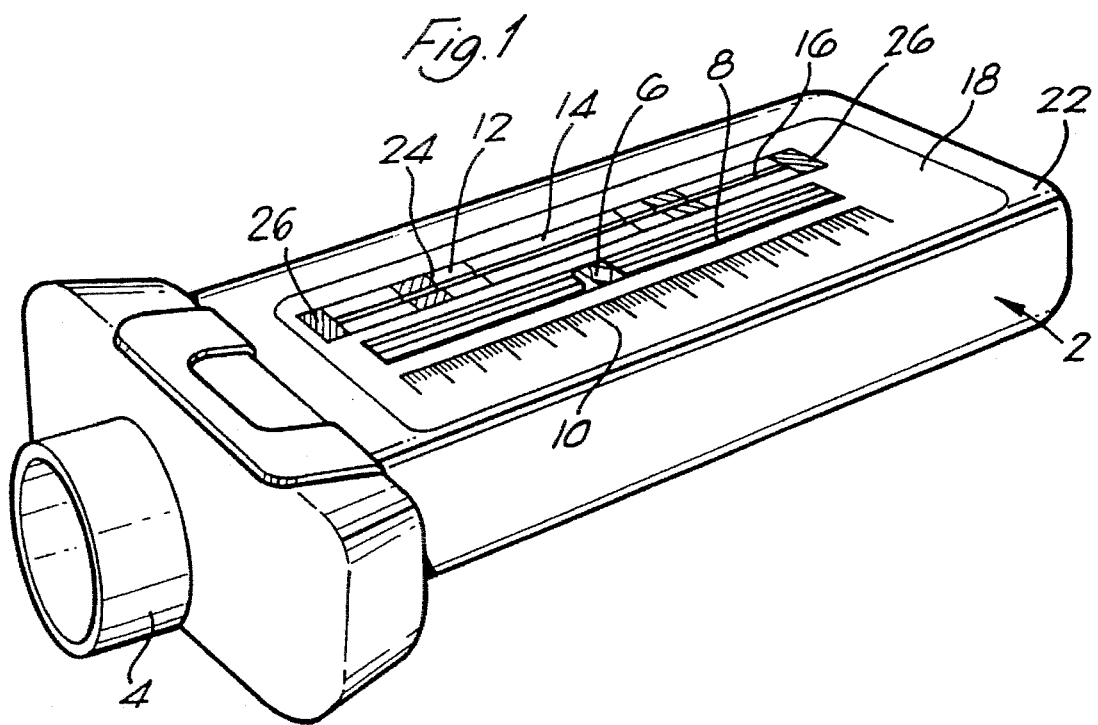

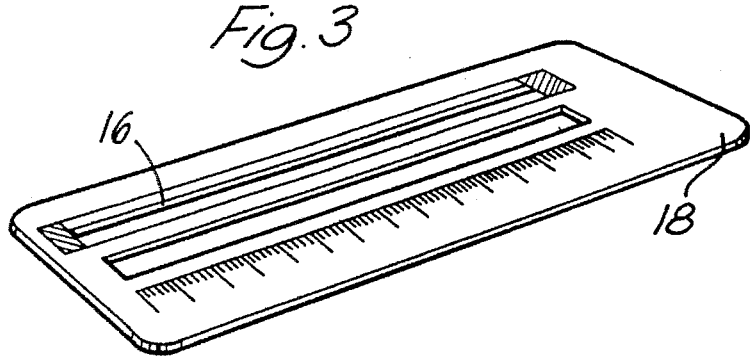
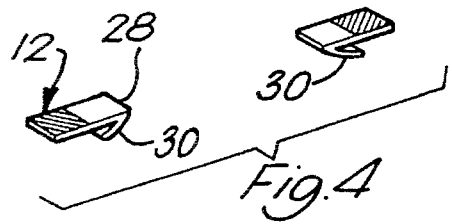
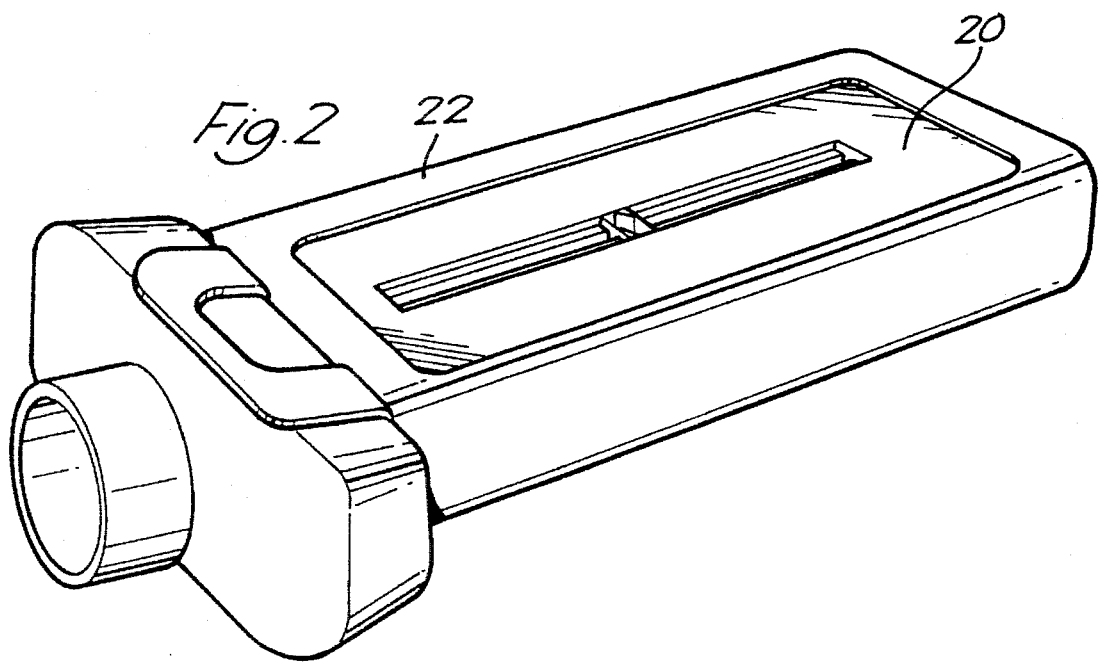

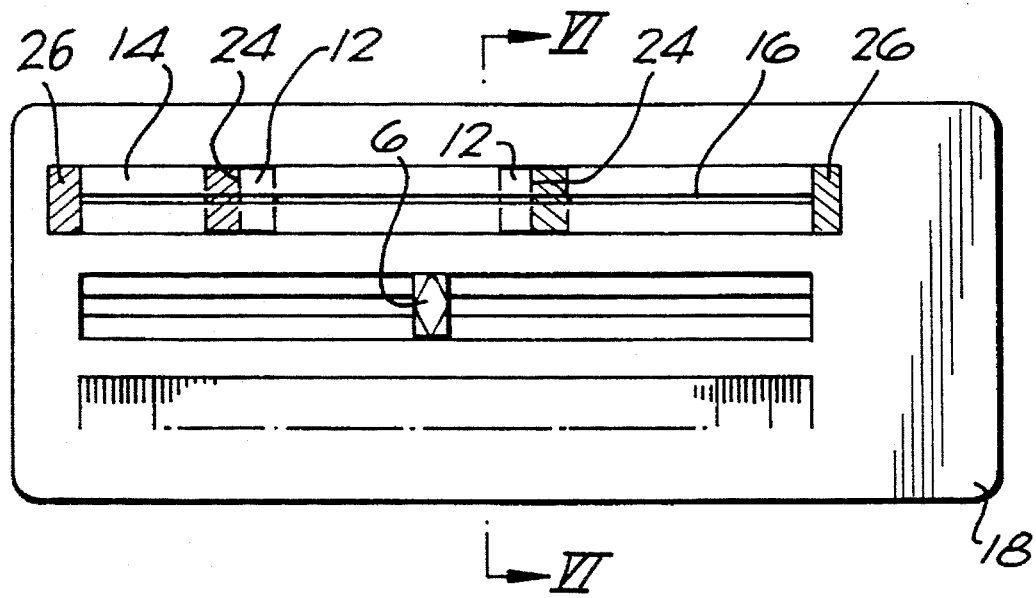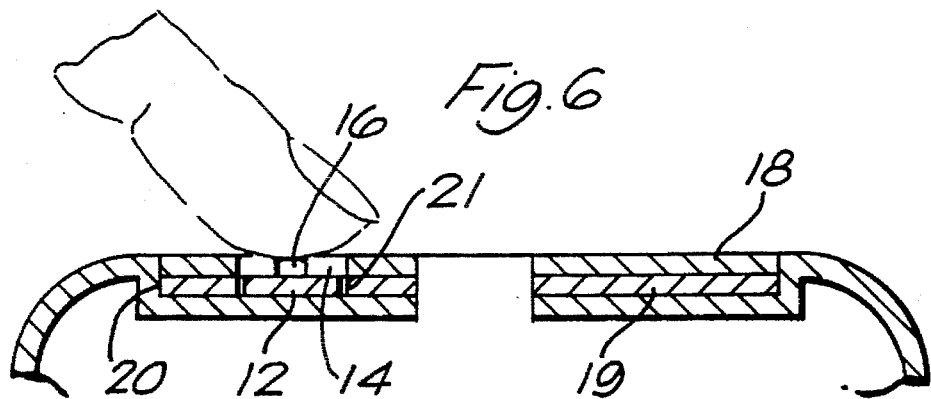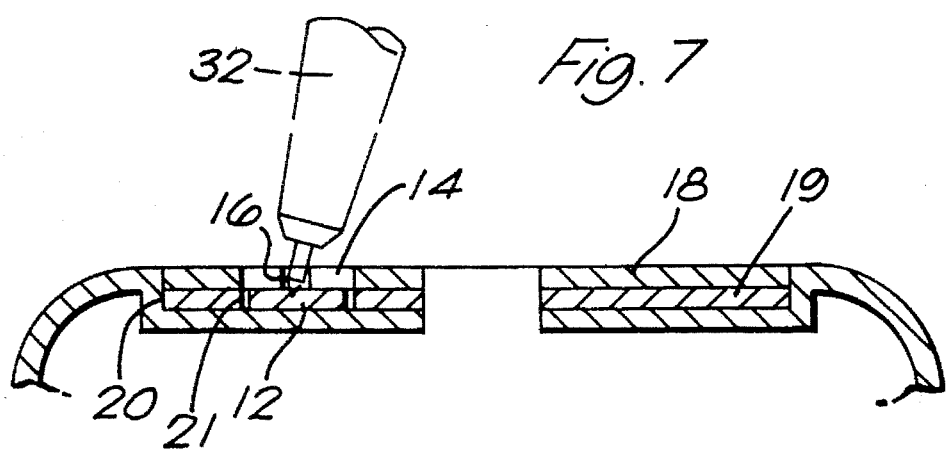

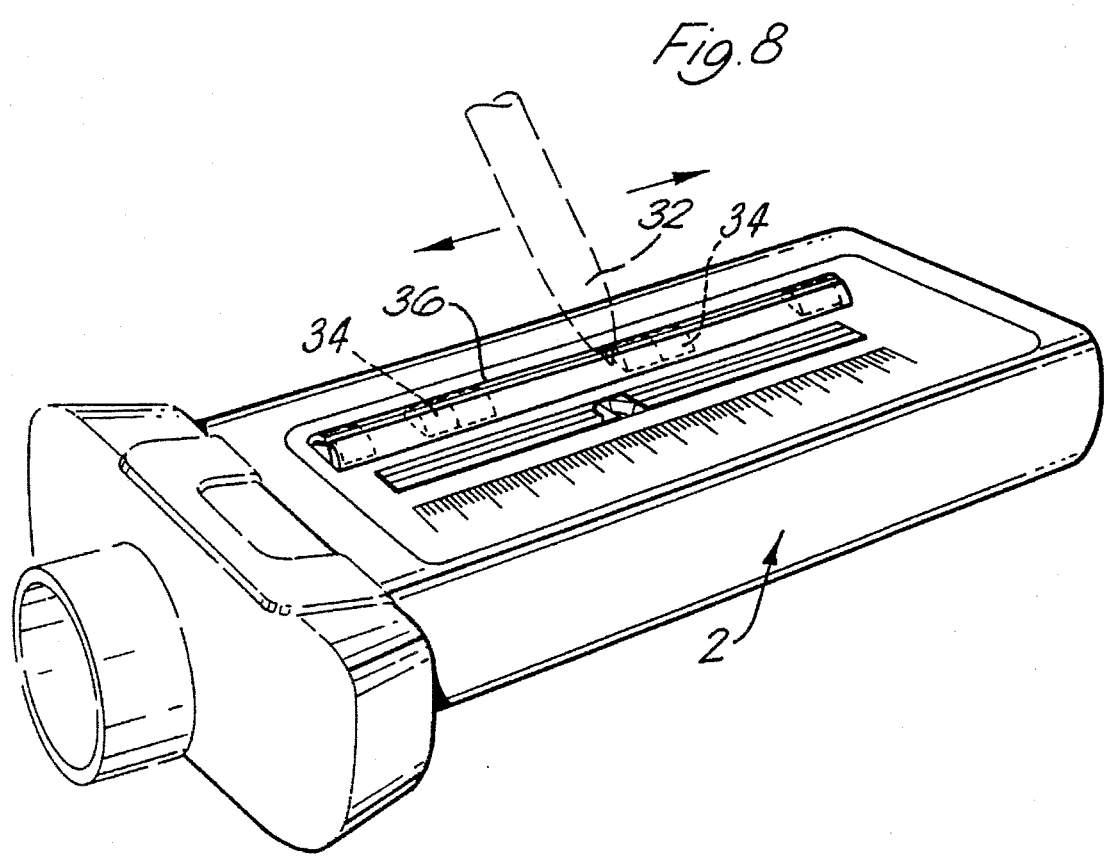

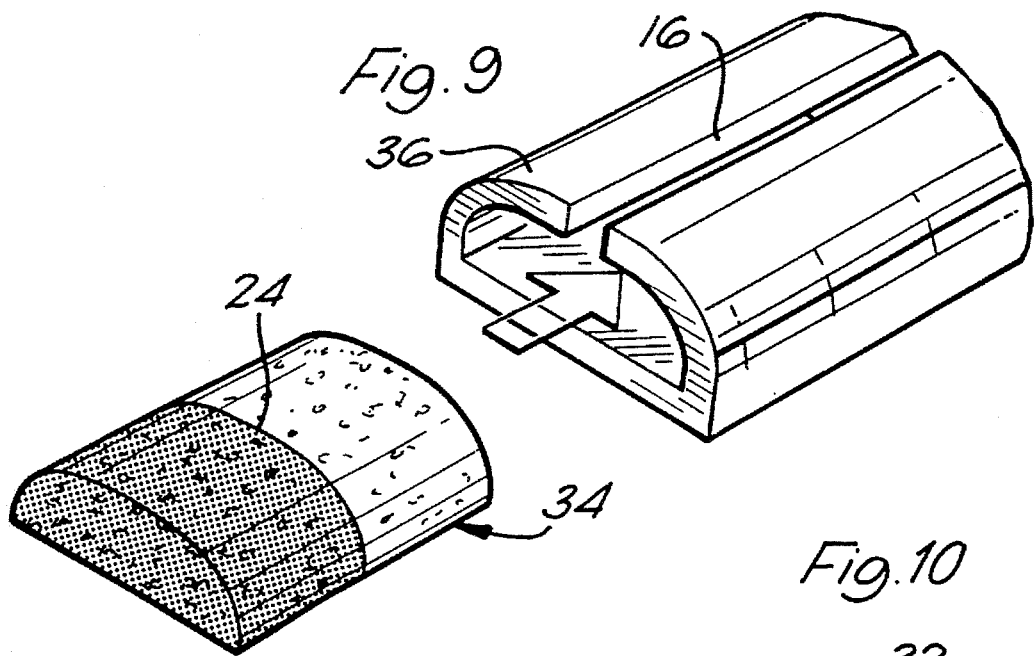
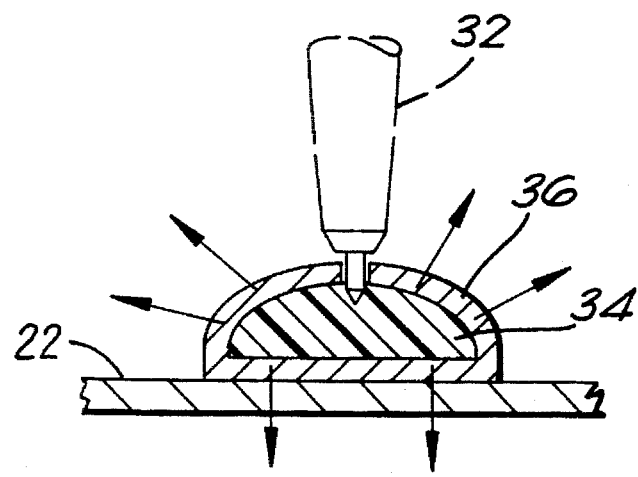
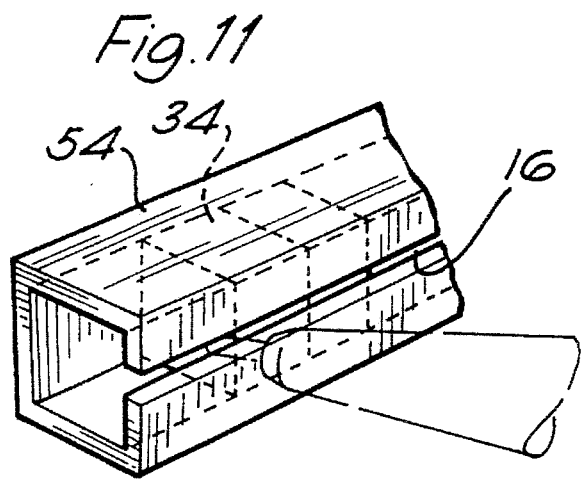

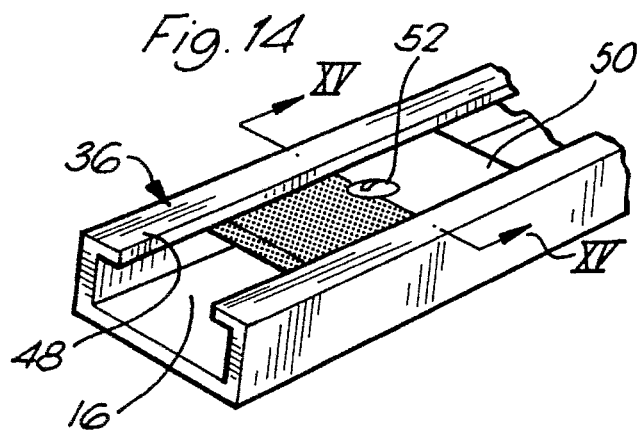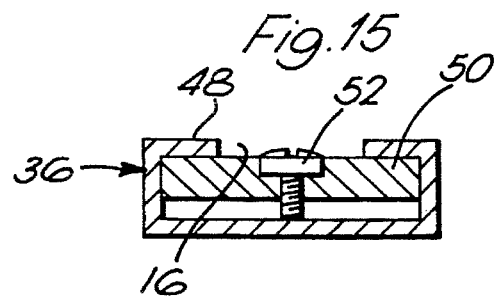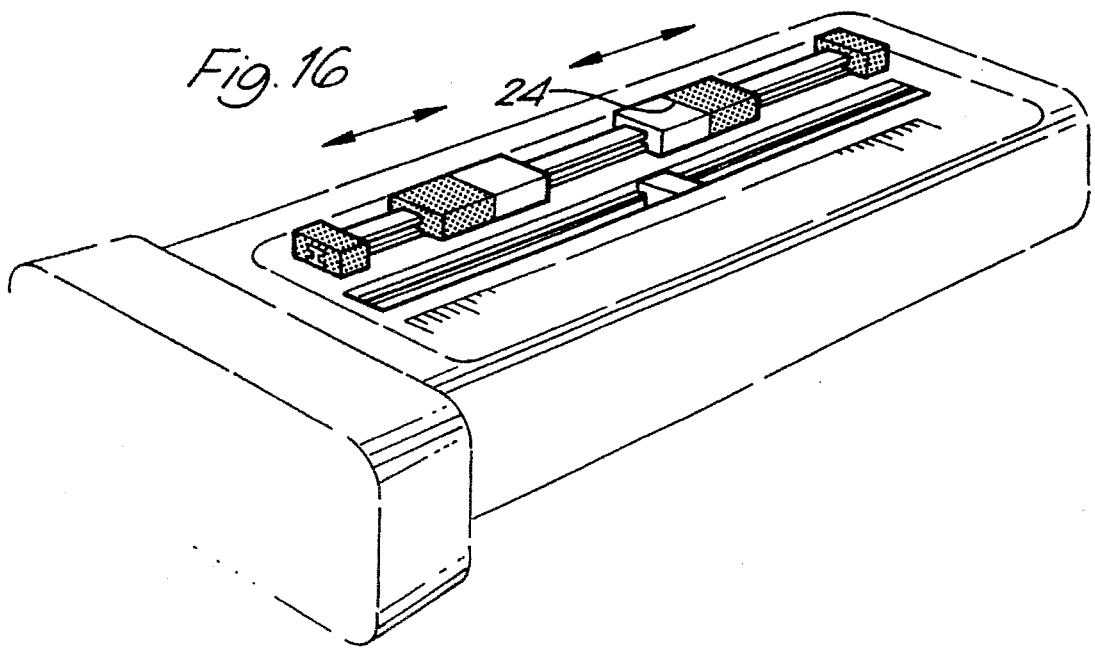

PEAK FLOW METERS

FIELD OF THE INVENTION

This invention relates to peak flow meters, by which term is meant devices for measuring the peak expiratory flow of air from a patient forcibly exhaling into an inlet of the meter.

DESCRIPTION OF RELATED ART

Peak flow meters are well known and widely used for monitoring the lung function of asthmatics. A typical basic device of this type is described in U.S. Pat. No. 4,041,935.

By means which are well-known, and which do not form part of the present invention, a pointer of the meter is driven from a manually-resetable zero position to a position corresponding to the maximum rate of flow of air during a single exhalation. Usually the pointer moves along a channel alongside which is a calibrated scale, enabling the patient to make a physical note of successive readings reached by the pointer, in order to monitor changes in lung function, such as might be caused by asthma or other respiratory ailment.

The difficulty with merely noting numbers is that patients are inefficient at doing it, the stored readings can be lost even if they are taken, and in either case incorrect readings may be made.

EUR. Respir. J., Number 5, 1992, prints under the title "International Asthma Report" a paper which provides an overview of current asthma management. Pages 621 and 622, of this journal, in a section entitled 'An Asthma Management Zone System for Patients', make reference to the use of colours associated with the position attained by the pointer of a peak flow meter. The colours are stated as being green, yellow and red, and each colour is associated with a range of movement of the pointer. Thus when the pointer comes to rest at a maximum flow rate lying within the green zone, this indicates satisfactory lung function. When it comes to lie within the yellow zone, this shows that some remedial treatment of the asthma giving rise to the impaired function might be necessary, whereas when the pointer comes to rest in the red zone this indicates that remedial action is essential, which might include hospitalization and the administration of oxygen.

A problem with application of the zone system in practice is that the positioning of the zones will vary from patient to patient, and so cannot be pre-set on a peak expiratory flow meter, e.g. printed by the calibrators.

An approach by solving this problem has been developed by Center Laboratories, a division of EM Industries Inc. in the USA, and is available under the trade mark ASTECH. In a standard peak flow meter construction, three slidable pointers (one green, one red, and one yellow) are arranged opposite the calibrated scale. Each may be positioned by the physician or asthma nurse to set the ranges for a given patient, but the patient may well become confused as to whether the yellow or cautionary zone extends to one or both sides of the central yellow pointer. This is confusing, and can lead to misreading by the patient with potentially adverse results. This known peak flow meter thus provides an ambiguous display, since the pointers do not adequately define one or both limits of the "coloured zones". GB-A-2247838 and International Publication WO 93/06778 describe similar approaches, both suffering from the same disadvantage of an ambiguous display.

SUMMARY OF THE INVENTION

In accordance with the present invention, a peak flow meter with two or more auxiliary indicators positioned on its face alongside the channel in which the meter pointer moves has each indicator in two colours with a sharp boundary between them. Two adjacent indicators have adjacent components of the same colour so that, for example, one indicator may mark the lower end of a green zone and the upper end of a yellow zone, while the other indicator indicates the lower end of the yellow zone and the upper end of a red zone. In a preferred form of the meter according to the present invention the positions of the indicators are preset, and they cannot be moved from their set positions without the use of a tool, so that a patient cannot accidentally mislead himself by accidentally or deliberately moving one of the indicators from its set position using a finger.

The peak flow meters of the present invention will generally have two or three indicators defining three or four zones respectively. Three zones are, as indicated above, standard for asthma management, but in some cases four may be useful and preferred for certain patients requiring very careful monitoring.

Accordingly it is a basic feature of all the peak flow meters according to the present invention that all three or more zones are of adjustable length, the one or more non-end zones being defined by the spacing between two indicators, and a subsidiary feature that the indicators which define the zones, are guarded from being touched directly.

The indicators, in practical embodiments of the invention, are preferably located in a channel or track adjacent the path movement of the pointer, and usually conveniently the opposite side to the calibrated scale. Such a channel or track arrangement is preferably built into the meter housing but it is within the scope of the present invention to convert a known type of peak flow meter to one according to the invention by affixing to it, e.g. adhesion, an elongate track or rail embodying the indicators, preferably in a fashion enabling their position along the track or rail only to be easily changed by using an appropriate tool.

BRIEF DESCRIPTION OF THE DRAWINGS

The present invention will now be described by way of example with reference to the accompanying drawings, in which:

FIG. 1 is a perspective view of a preferred embodiment of a peak flow meter of the present invention lying on its back with its face uppermost;

FIG. 2 is a view similar to FIG. 1 but with the fascia panel removed;

FIG. 3 is a similarly-oriented view of the fascia panel itself;

FIG. 4 is a similarly-oriented view of two sliders intended to be positioned between the fascia panel of FIG. 3 and the body of FIG. 2;

FIG. 5 is a plan view of the fascia panels shown in FIG. 3 when in position on a peak flow meter, with the rest of the meter not being shown;

FIG. 6 is a diagrammatic view of the fascia panel shown in FIG. 5, showing how the two auxiliary indicators cannot be displaced solely by fingertip pressure;

FIG. 7 is a diagram of similar to FIG. 6, showing how each indicator may be displaced by means of a tool, such as the uncapped end of a ball pen;

FIG. 8 is a view similar to FIG. 1 of a peak flow meter with another form of auxiliary indicators;

FIG. 9 is a diagrammatic view, on a larger scale, of one indicator shown in FIG. 8 with its associated housing;

FIG. 10 is an end view of the indicator of FIG. 9 shown in place in its housing, and indicating how it may be moved axially by means of an uncapped writing implement;

FIG. 11 is a diagrammatic perspective view of another form of auxiliary indicator and its housing;

FIG. 14 is a view similar to FIG. 9 of another embodiment of indicator with its housing;

FIG. 15 is a section along the plane XV–XV of FIG. 14, and

FIG. 16 is a diagrammatic perspective view of the indicators of FIGS. 14 and 15 with their housings removed.

DESCRIPTION OF THE PREFERRED EMBODIMENTS

Figure 12:
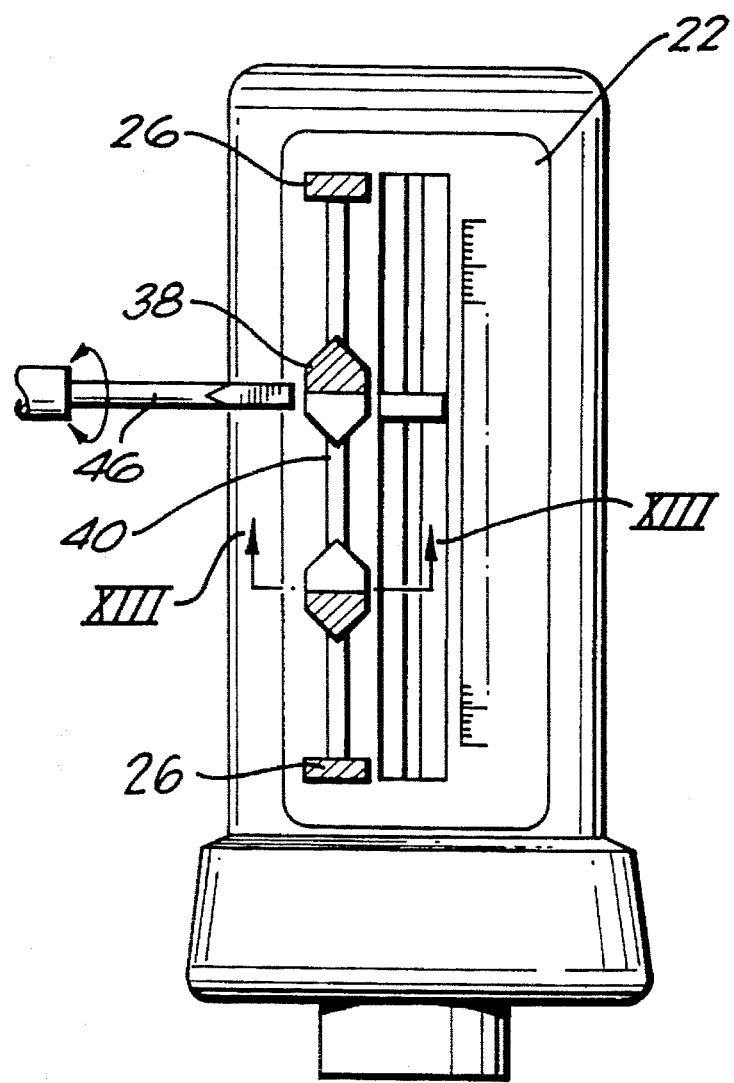
FIG. 12 is a front view of a peak flow meter fitted with yet another type of auxiliary indicator.

FIG. 1 of the drawings shows the housing of a peak flow meter 2 having a hollow inlet 4 into which is inserted a separate tube (not shown), either a disposable cardboard tube or a plastics tube which the patient who is having his lung function measured grips with his lips in order to exhale as forcibly as possible into the flow meter. By means which are known in themselves, and which therefore will not be described herein in any further detail, the flow of exhaled air from the patient causes a pointer 6 to move along the length of a channel 8 in the upper (as viewed) wall of housing 2. Before the reading was taken, the patient or operator manually moved the pointer 6 to that end of channel 8 which is nearer inlet 4. The distance which this pointer moves on each breath from the reference position is a function of the maximum rate of flow of exhaled air. As is usual, extending along one side of channel 8 is a graduated scale 10, which permits a numerical value to be given to the position of pointer 6. On the other side of channel 8 is disposed a pair of movable indicators 12 overlain by a length of transparent or translucent material 14 in which is a slot 16. The strip 14 may be integral with a fascia panel 18 let into a recess 20 (see FIG. 2) in wall 22 of the housing.

In accordance with the invention, each indicator 12 has two areas of different colour, or which are otherwise visually-distinguishable, forming a straight boundary 24. If the peak flow meter 2 is using the convention already discussed of green for the safe region of peak flow yellow for the caution region of peak flow, and red for the danger region, then the indicator 12 further from inlet 4 has one half coloured green and the other half colour yellow, while the nearer indicator has one half coloured yellow and the other half coloured red, with the yellow portions of both indicators facing each other. The end of the strip 14 may be marked by end regions 26, of which one may be coloured green and the other coloured red, so that the user of the meter can see at a glance after he has used the meter, in which region (on the left-hand side of the channel 8 as viewed) pointer 6 has come to lie. A person suffering from asthma or other respiratory complaint need not concern himself with the actual numerical reading associated with the position of pointer 6, but only has to take any remedial action if the pointer is beside the yellow or red regions.

The indicators 12 are intended to be very difficult or impossible to move manually with the fingertips or a fingernail, and thus cannot be moved accidentally by the meter housing being knocked or shaken. To ensure this, as easiest seen in FIGS. 6 and 7, the slot 16 is narrow and the thickness of strip 14 or fascia plate 18 is sufficient to space the outer face of an indicator so that it cannot be contacted with a fingertip. Fascia plate 18 is adhered in recess 20 via a double sided adhesive panel 19 of shape similar to plate 18 but with a wider channel 21 which underlies strip 14. Each indicator 12 is a friction or other fit in the channel 21 along which it may move between the fascia plate 18 and the wall of recess 20. In order to adjust the position of either indicator, it is necessary for a pointed tool or instrument, such as a nail file or screwdriver, or uncapped end of a ball pen, to be inserted into slot 16 sufficiently far to contact the respective end face of the indicator to be moved. The tool or instrument is then moved in the appropriate direction to align the respective boundary 24 with the intended transition point between the two regions associated with the indicator. Removal of the tool ensures that the position of indicator 12 remains fixed until it next needs to be adjusted. The actual position of each indicator may be chosen at first by a physician and may be adjusted by the user after sufficient use of the meter as indicated where the indicator should be placed to give him the daily guidance he might need in monitoring his lung function.

As shown in FIG. 4, each indicator may take the form of a laminar piece of resilient metal or plastics material, having an integral folded-over flap 30 intended to come into frictional contact with the wall of recess 20 when the indicator is pressed towards it by fitting of the fascia plate 18 in place. The dimensions of flap 30 are related to the thickness of the channel 21 in which the indicator may move, so that sufficient frictional force is applied to keep the indicator in place against the fascia plate despite impact and acceleration forces to which it might be accidentally subjected in use. However, the frictional force can be overcome, as discussed above, by force applied to the respective end face of the main body 28 of indicator 12 by means of an appropriate tool. In place of a folded-over flap, the indicator may simply be made of an appropriate thickness material e.g. fractionally thicker than the thickness of double-sided adhesive panel 19. This is preferred for ease of manufacture.

FIG. 5 shows a plan view of the fascia plate 18 of FIG. 3 in position on a flow meter. In all the drawings, those components which are common to two or more drawings retain the same reference.

FIG. 6 and 7 are diagrammatic sectional views along line VI—VI of FIG. 5. FIG. 6 shows how the thickness of fascia plate 18 prevents a finger from coming into contact with indicator 12, whereas this contact can be achieved, as shown in FIG. 7, by means of a ball pen 32 having its uncapped end inserted into and through slot 16 so that it contacts the respective side face of indicator 12.

In that alternative form of the invention shown in FIG. 8, which shows a known peak flow meter retrofitted with an indicator strip, each indicator 12 takes the form of a plug 34 of resilient material movable along the length of a D-sectioned channel 36 having slot 16 extending along its crest. Each plug 34 may take the form of two self-coloured bodies of resilient plastics material bonded together to form the desired boundary 24. The channel 36 may be of metal or plastics material, and may be formed by extrusion. The channel is glued or otherwise secured to face 22 of meter 2.

The normal cross-sectional shape of indicator 34 is greater than that presented by channel 36, so that the plug 34 has to be partly compressed in order to insert it into channel 36, as can be seen from FIG. 9. The natural resilience of the material forming plug 34 ensures that it grips the internal surfaces of channel 36 with sufficient frictional force to keep it in place during normal use of the meter. As already mentioned, this frictional force may be overcome by means of a pen 32 or other tool inserted into slot 16. This jamming of plug 34 in channel member 36 is indicated diagrammatically in FIG. 10.

FIG. 11 is a view of an alternative to that form of the invention shown in FIGS. 8 to 10. In this Figure, the channel 36 is replaced by a square channel 54 of transparent material, which is glued or otherwise secured to the meter housing so that a slot 16 is in a side face of channel 54, rather than in its top face. Positioned within channel 54 is a rectangular-sectioned plug of material similar to plug 34, with this plug having to be compressed somewhat before it can be inserted into channel 54.

Figure 13:
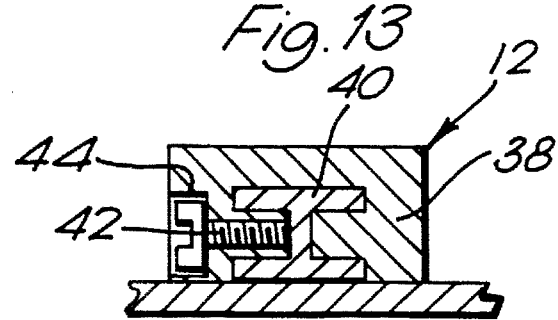
FIG. 13 is a diagrammatic section along line XIII—XIII of FIG. 12.

In that form of the invention shown in FIGS. 12, 13 and 16, the indicators 12 take the form of bi-coloured blocks of plastics or like material 38 movable along the length of an H-sectioned rail 40 held in place against face 22 of the meter by coloured end blocks 26. Because, as shown in FIG. 13, each block 18 has formed within it a recess of complementary shape to rail 40, the block cannot be lifted from the rail. In addition, each block has a screw 42 threaded in it, with the head of the screw being located in a recess 44 so that the screwhead cannot be gripped manually. Instead, as shown in FIG. 12, a screwdriver 46 has to be used to release screw 42 to enable the indicator 12 to be moved to an alternative position along rail 40.

FIGS. 14 and 15 show an alternative to that embodiment shown in FIGS. 8 to 10, in that the channel 36 has a cross-section in the shape of a square C, so that the opposing flanges 48 of the channel define a relatively-wide slot 16 between them. Moving in the channel is a rectangular piece 50 of rigid material presenting the two differently-coloured regions to slot 16. Screw-threaded in piece 50 is a screw 52 having its head lying relatively flush with the outer surface of piece 50, and with the end of its shank bearing on the inner surface of channel 36. Preferably the screw 52 is held captive in piece 50 so that rotation of the screw 52 in the appropriate direction by means of a screwdriver (not shown) is effective to force the piece 50 into frictional engagement with the undersurfaces of flanges 48.

Accordingly it will be seen that the present invention provides a peak flow meter with zone indicators which clearly show a boundary between two visually-distinguishable zones, and in which each indicator can have its position adjusted relatively to the path of a pointer only by means of a tool. All of the embodiments illustrated show three-zone meters; a four zone meter, e.g. with zones coloured green, yellow, red and purple, with green/yellow, yellow/red and red/purple movable boundary indicators may be constructed analogously.

I claim:

1. In a peak flow meter including a meter housing having a face, a channel, a pointer movable along the channel from a start position by a distance which is dependent on the lung function of a patient and, positioned adjacent to the channel, at least two indicators, each indicator being movable independently along an axis substantially parallel with that of the channel and along which each indicator can be displaced axially to vary its position, the improvement consisting of each indicator displaying a boundary between two visually-distinguishable areas.

2. The peak flow meter of claim 1, in which each indicator is of fixed dimensions, and is held in place by friction, with each indicator being shielded from direct contact by means of a cover layer having therein a longitudinally-extending slot through which a tool can be inserted to contact the indicator in order to displace the indicator axially, whereby axial displacement of each indicator can be achieved only by the use of a tool.

3. The peak flow meter of claim 2, in which at least a portion of the cover layer is made of a transparent or translucent material having a slot which extends across the indicators.

4. The peak flow meter of claim 2, in which the cover layer is integral with a fascia plate positioned in a recess in the face of the meter housing, said fascia plate having an outer surface and an undersurface opposite thereto and adjacent the meter housing, whereby each indicator is in frictional engagement with the undersurface of the fascia plate and the recess in the housing.

5. The peak flow meter of claim 4, in which each indicator is in the form of a laminal body either having an integral turned-over flap of resilient material or being of sufficient thickness to be a friction fit between the fascia plate and the face of the housing.

6. The peak flow meter of claim 1, further including a hollow channel secured to the face of the meter housing and in which each indicator takes the form of a body of material movable along the length of the hollow channel.

7. The peak flow meter of claim 6, in which each indicator includes a screw movable from one position in which the indicator is kept in place in the housing to another position in which the indicator is movable with respect to the housing.

8. The peak flow meter of claim 6, in which each indicator takes the form of a body of resilient material having a natural cross-sectional area greater than a cross-sectional area of the hollow channel, whereby each indicator is held in place by frictional forces resulting from compression which is necessary to insert each indicator into the channel.

9. The peak flow meter of claim 1 including a rail, and in which each indicator is in the form of a body of rigid material slidable along the length of the rail, each indicator partially embracing the rail and including means by which the indicator can be locked in place at any desired point along the length of the rail.

* * * * *